United States Patent
Weiner

[19]

[11] Patent Number: 6,056,748
[45] Date of Patent: May 2, 2000

[54] MODULAR FIXATOR ASSEMBLY

[76] Inventor: Lon S. Weiner, 5 Horizon Rd., #2809, Fort Lee, N.J. 07024

[21] Appl. No.: 09/026,791

[22] Filed: Feb. 20, 1998

[51] Int. Cl.$^7$ ................................................ A61B 17/60
[52] U.S. Cl. ............................................. 606/55; 606/54
[58] Field of Search ................................ 606/54, 55, 56, 606/57, 58, 59

[56] References Cited

U.S. PATENT DOCUMENTS

| | | |
|---|---|---|
| 4,548,199 | 10/1985 | Agee . |
| 4,611,586 | 9/1986 | Agee et al. . |
| 4,628,919 | 12/1986 | Clyburn . |
| 4,662,365 | 5/1987 | Gotzen et al. ............................ 606/54 |
| 4,730,608 | 3/1988 | Schlein . |
| 4,848,327 | 7/1989 | Perdue . |
| 4,889,111 | 12/1989 | Ben-Dov ................................ 606/54 |
| 4,922,896 | 5/1990 | Agee et al. . |
| 5,087,258 | 2/1992 | Schewior ................................ 606/56 |
| 5,527,309 | 6/1996 | Shelton .................................. 606/55 |
| 5,620,442 | 4/1997 | Bailey et al. . |
| 5,658,283 | 8/1997 | Huebner . |
| 5,662,649 | 9/1997 | Huebner . |
| 5,683,389 | 11/1997 | Orsak .................................... 606/54 |
| 5,810,814 | 9/1998 | Newson .................................. 606/54 |
| 5,827,283 | 10/1998 | Groiso et al. ........................... 606/54 |

*Primary Examiner*—Michael Buiz
*Assistant Examiner*—Daphna Shai
*Attorney, Agent, or Firm*—Mathews, Collins, Shepherd & Gould, P.A.

[57] ABSTRACT

A modular fixator assembly capable of allowing motion at the wrist during treatment of wrist fractures. The fixator assembly includes a distractor device, a pin outrigger attached to the distrator device, at least one pin for fixating the fracture fragments, and pin clamping assemblies for attaching the pin to the outrigger. The outrigger conforms to the anatomical configuration of the fractured bone thereby enabling direct fixation of the fracture fragments.

21 Claims, 9 Drawing Sheets

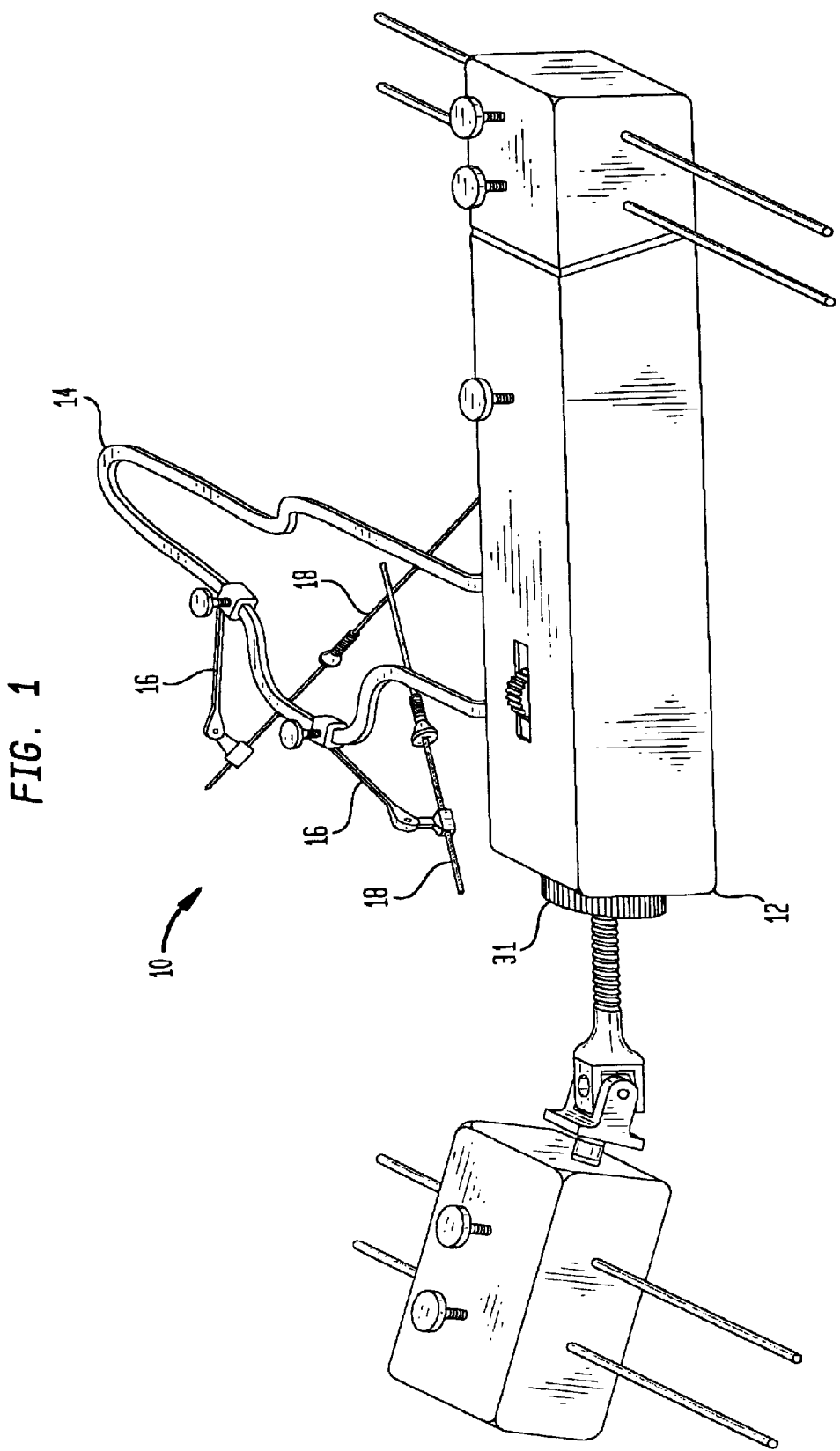

MODULAR FIXATOR ASSEMBLY

FIELD OF THE INVENTION

This invention relates to external bone fixators for setting fractures of the human skeleton and, in particular, to a modular bone fixator assembly for setting fractures of the distal radius and other bones.

BACKGROUND OF THE INVENTION

The prior art is replete with external bone fixator devices which are used for setting various bone fractures. Practically all external bone fixator devices employ transcutaneous pins or screws which are secured in the bone on either side of the fracture. The pins are typically attached to an external splint device which adjusts the relative positions of the pins using various articulations. The fixator allows the bone pieces at the fracture to be realigned by a surgeon. Once the bone pieces have been realigned, the articulations in the fixator are locked in place to maintain the bone alignment.

Many of these external bone fixator devices are especially adapted for repairing fractures of the distal radius. This type of fracture generally involves a fracture site close to the distal head of the radius. Such fractures are typically reduced using pins set in the metacarpal bone and pins set on the proximal side of the fracture in the distal half of the radius.

It has been recognized that it is desirable for the wrist to have a certain degree of mobility during the treatment of wrist fractures. However, prior art fixator devices which employ longitudinal traction applied by proximal and distal pins do not allow motion at the wrist without crossing the joint during the period of fracture immobilization.

Accordingly, there is a need for an improved fixator device which is capable of allowing motion at the wrist during treatment of fractures of the distal radius and other bones without crossing the affected joint.

SUMMARY

The present invention is directed to a modular fixator assembly capable of allowing fixation to be confined to the affected bone as well as spanning capabilities thus, allowing motion at the wrist during treatment of fractures of the distal radius and other bones. The fixator assembly comprises a distractor device for providing distracton of a fractured bone, a pin outrigger attached to the distrator device, for enabling fixation of the fracture fragments of the fracture bone, at least one pin for fixating the fracture fragments, and clamping means for attaching the pin to the outrigger. The outrigger conforms to the anatomical configuration of the fractured bone thereby enabling direct fixation of the fracture fragments.

BRIEF DESCRIPTION OF THE DRAWINGS

The advantages, nature and various additional features of the invention will appear more fully upon consideration of the illustrative embodiments now to be described in detail in connection with the accompanying drawings. In the drawings:

FIG. 1 is a perspective view of the modular fixator assembly of the present invention;

DETAILED DESCRIPTION

Figure 2A:
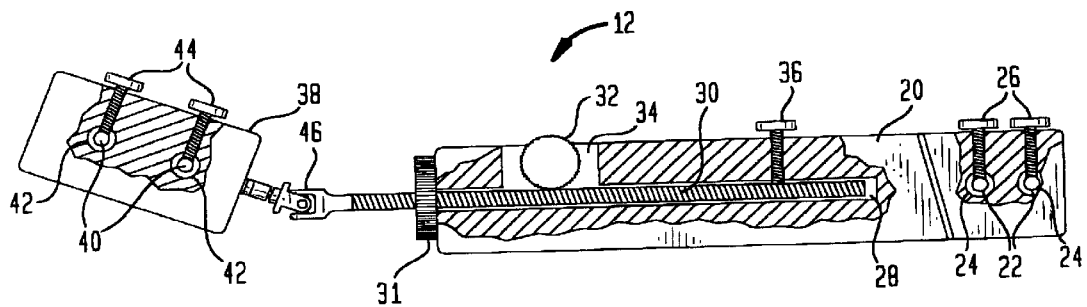
FIG. 2A is a partially sectioned, elevational side view of the distractor device shown in FIG. 1.

FIG. 1 is a perspective view of the modular fixator assembly 10 according to an embodiment of the invention. The assembly 10 includes a distractor device 12, a pin outrigger 14 removably attached to the distractor device 12, and one or more outrigger pins 18 attached to the outrigger by pin clamp assemblies 16. The fixator assembly 10 is generally used for repairing fractures of bones, especially fractures of the distal radius.

FIG. 2A is an elevational side view, partially in section, of the distractor device 12. An elongated proximal pin clamp member 20 forms the proximal portion of the distractor device 12. Proximal transcutaneous pins 22 are adapted to extend through transverse openings or apertures 24 in the proximal pin clamp member 20. The proximal pins 22 may be secured in place by set screws 26. The distal end of the proximal pin clamp member 20 includes a closed-ended bore 28 which extends axially therethrough and terminates near the proximal end thereof. The bore 28 receives an externally threaded rod 30. A thumb screw 31 threadedly attached to the externally threaded rod 30 allows a surgeon to selectively extend or retract the rod 30. The position of the rod 30 can be locked via a rod set screw 36. A thumb gear 32, for distal/proximal adjustment of the pin outrigger 14, is rotatively disposed within the proximal pin clamp member 20. The thumb gear 32 extends through an elongated slot 34 defined in the surface of the proximal pin clamp member 20.

A distal pin clamp member 38 forms the distal portion of the distractor device 12. Distal transcutaneous pins 40 are adapted to extend through transverse openings or apertures 42 in the distal pin clamp member 38. The distal pins 40 can be secured in place by set screws 44. A universal joint 46 couples the proximal end of the distal pin clamp member 38 to the distal end of the threaded rod 30. The universal joint 46 allows universal pivotal movement of the distal pin clamp member 38 relative to the proximal pin clamp member 20.

Figure 2B:
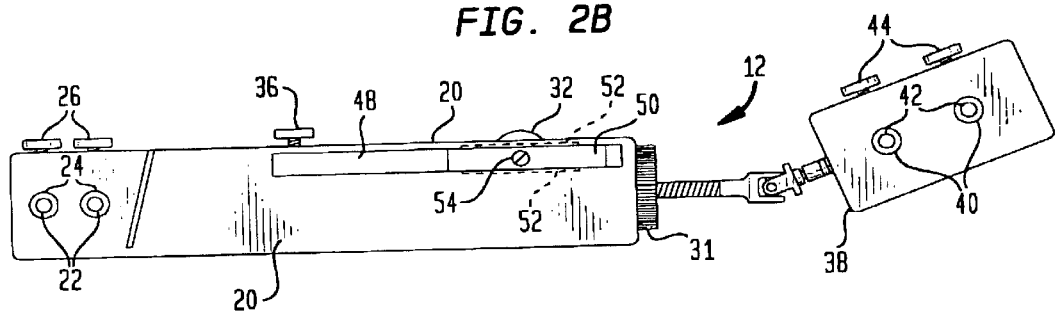
FIG. 2B is an elevational side view from the outrigger side of the distractor device shown in FIG. 1.

FIG. 2B is an elevational side view depicting the outrigger side of the distractor device 12. An undercut, elongated groove 48 extends partially along a side of the proximal pin clamp member 20. A slidably adjustable outrigger mounting member 50 rides in the groove 48. The mounting member 50 attaches the outrigger 14 to the proximal pin clamping member 20. The mounting member 50 includes outwardly extending flanges 52 (shown with broken lines) that are slidably retained in the undercut groove 48. The mounting member 50 is adapted to be incrementally adjusted in the distal/proximal direction (relative to the proximal pin clamping member 20) with the thumb gear 32. The proximal and distal location of the mounting member 50 may be locked via a set screw 54. In one embodiment, the groove 48 allows approximately 15 mm of proximal and distal adjustment of the outrigger mounting member 50.

Figure 2C:
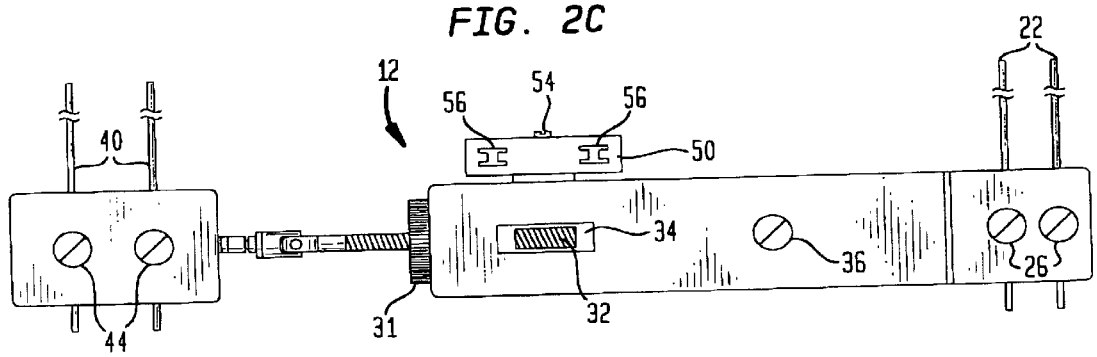
FIG. 2C is a top plan or dorsal view of the distractor device shown in FIG. 1.

FIG. 2C is a dorsal view of the distractor device 12. This view shows a pair of I-shaped apertures 56 which extend through the mounting member. The I-shaped apertures 56 receive mounting arms provided on the outrigger 14 as will be explained further on.

Figure 3A:
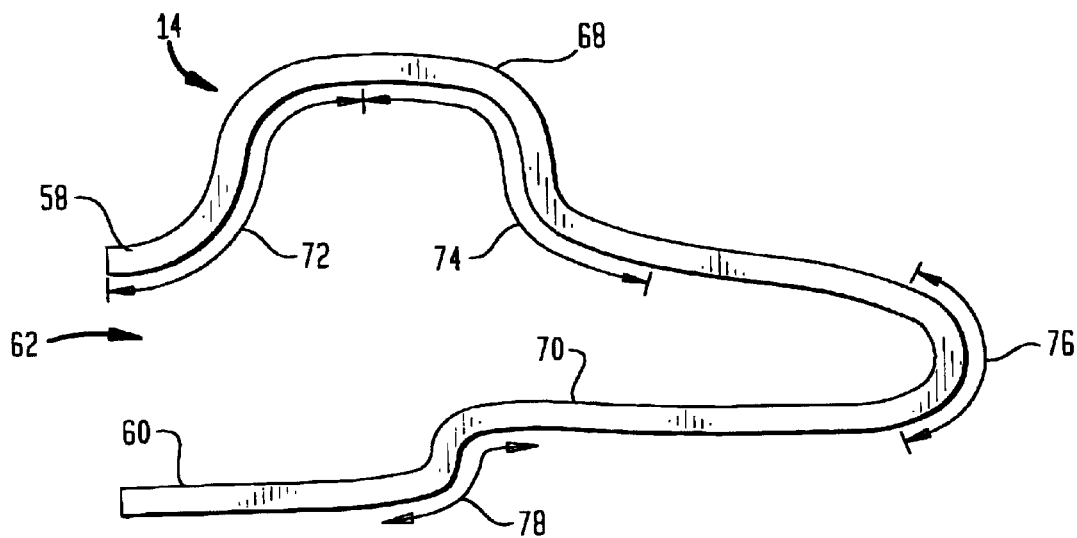
FIG. 3A is a top plan or dorsal view of the pin outrigger shown in FIG. 1.
Figure 3B:
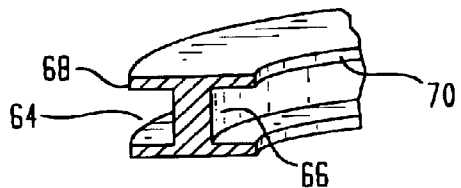
FIG. 3B is a cross-sectional view through a segment of the outrigger shown in FIG. 1.

FIG. 3A is dorsal view of the outrigger 14. The outrigger 14 includes first and second projecting elements 58, 60 which extend from the mounting end 62 of the outrigger 14. FIG. 3B is a cross-sectional view which shows outer and inner side grooves 64, 66 that extend continuously along respective outer 68 and inner side surfaces 68, 70 of the outrigger 14. The grooves 64, 66 provide the outrigger with an I-shaped cross-section and enable the pin clamp assemblies 16 to be slidably mounted to the outrigger 14 as will be explained further on.

The first projecting element 58 shown in FIG. 3A, generally conforms to the anatomical configuration of the distal radius. Starting at the mounting end 62, the first projecting element 58 includes a first generally S-shaped section 72 which extends away from the second projecting element 60, mimicking the radial styloid. The first section 72 merges with a second generally S-shaped section 74 that extends back toward the second projecting element 60 to conform the element 60 to the coronal anatomy of the distal radius at the level of the wrist joint. The second S-shape section 74 converges with the second projecting 60 element at a generally C-shaped section 76 which corresponds to the level of the distal ulna joint.

The second projecting element 60 cooperates with the first projecting element 58 to stabilize and strengthen the outrigger 14. The second projecting element 60 extends from the C-shaped section 76 toward the mounting end 62. A jogged section 78 provided in the second projecting element 60 strengthens and stabilizes the element.

Figure 3C:
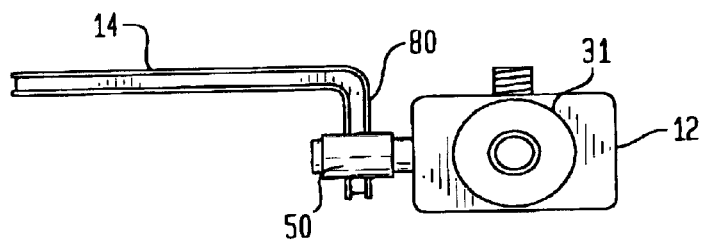
FIG. 3C is an elevational distal end view showing the outrigger mounted to the distractor.

FIG. 3C is an elevational distal end view of the outrigger 14 mounted to the distractor device 12. Each projecting member 58, 60 has a depending arm 80 (only the first projecting member is visible). Each arm 80 is removably received in a corresponding one of the I-shaped apertures 56 of the mounting member 50.

Figure 4A:
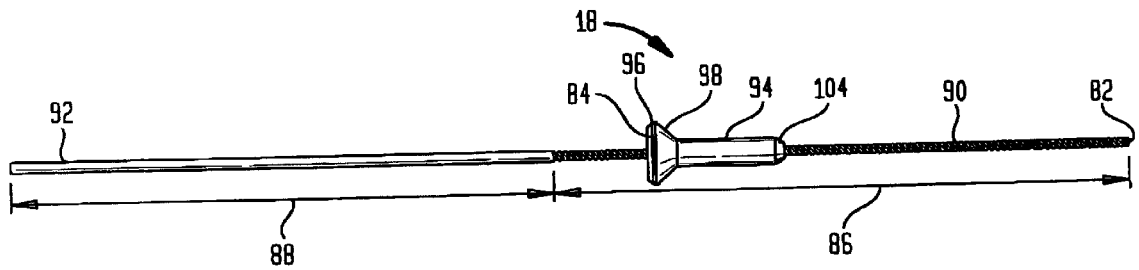
FIG. 4A is an elevational view of one of the outrigger pins shown in FIG. 1.

FIG. 4A is an elevational view of one of the outrigger pins 18. In the preferred embodiment, each outrigger pin 18 includes a pin member 82 and a tubular screw member 84. The pin member 82 has an anterior portion 86 and a posterior portion 88. The anterior portion 86 is circular in cross-section and includes a conventional self-tapping external thread 90. The posterior portion 88 is adapted to enable a chuck (not shown) to drive the pin member 82 into the bone fragments. This may be accomplish by providing the posterior portion 88 with a square or rectangular cross-section. In other embodiments, only the terminal end 92 of the posterior portion 88 is adapted to be driven by a chuck. In such embodiments the terminal end may be square or rectangular in cross-section and the remainder of the posterior portion can be circular in cross-section.

The tubular screw member 84 includes an elongated sleeve 94 and a enlarged head 96 with a frustoconical seating surface 98. The sleeve 94 includes a tapered lead-in surface 104 which facilitates entrance of the screw member 84 into a drilled bone fragment FIG. 4C is a cross-sectional view through the screw member 84. An opened ended bore 100 extends axially through the screw member 84. The bore 100 includes internal thread 102 that is adapted to engage the external thread 90 on the anterior portion 86 of the pin member 82. The diameter of the bore is sized to allow the posterior portion 88 of the pin member 82 to pass freely through the screw member 84.

Figure 4B:
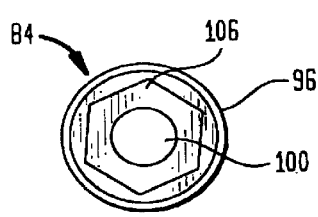
FIG. 4B is an elevational end view of the screw member of one of the outrigger pins shown in FIG. 1.
Figure 4C:
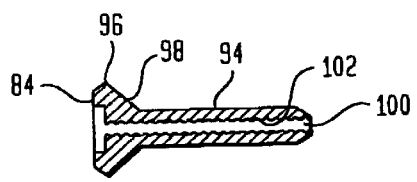
FIG. 4C is an axial cross-sectional view through the screw member.

FIG. 4B is an elevational end view of the screw member 84. The enlarged head 96 includes screw driving means 106 for threading the screw member 84. In the shown embodiment, the screw driving means 106 is constructed as a socket-like recess. The screw driving means 106 enables the screw member 84 to be driven with a correspondingly adapted screw driver.

Figure 5:
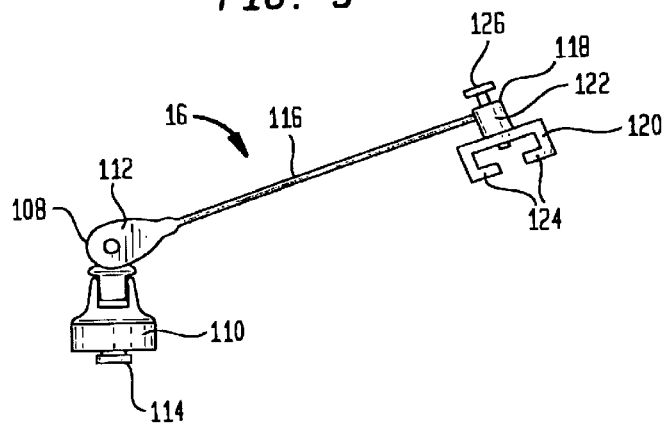
FIG. 5 is an elevational view of one of the outrigger pin clamp assemblies shown in FIG. 1.

FIG. 5 is an elevational view of one of the outrigger pin clamp assemblies 16. Each pin clamp assembly 16 includes a universal joint member 108 having pivotally coupled first and second joint elements 110, 112. The first joint element 110 is adapted for clamping the posterior portion of the pin member via a set screw 114. The second joint element 112 is coupled to one end of an elongated rod 116. The other end of the elongated rod 116 is coupled to a swiveling slide member 118 adapted to be slidably attached to the outrigger 14. The swiveling slide member 118 includes a C-shaped member 120 rotatively coupled to a rod attachment member 122. The C-shaped member 120 defines a pair of inwardly facing flanges 124 that are adapted to slide and be retained in the outer and inner grooves of the outrigger 14. The location of the slide member 118 on the outrigger 14 can be fixed with a set screw 126 that extends into the opening of the C-shaped member 120. The swiveling slide member 118 and the universal joint member 108 enable universal articulated movement of the pin clamp assembly 16. The pin clamp assembly 16 may be locked into position by locking means associated with each of the swiveling slide and universal joint members 118, 108. The locking means may include set screws or friction bushings.

Figure 6A:
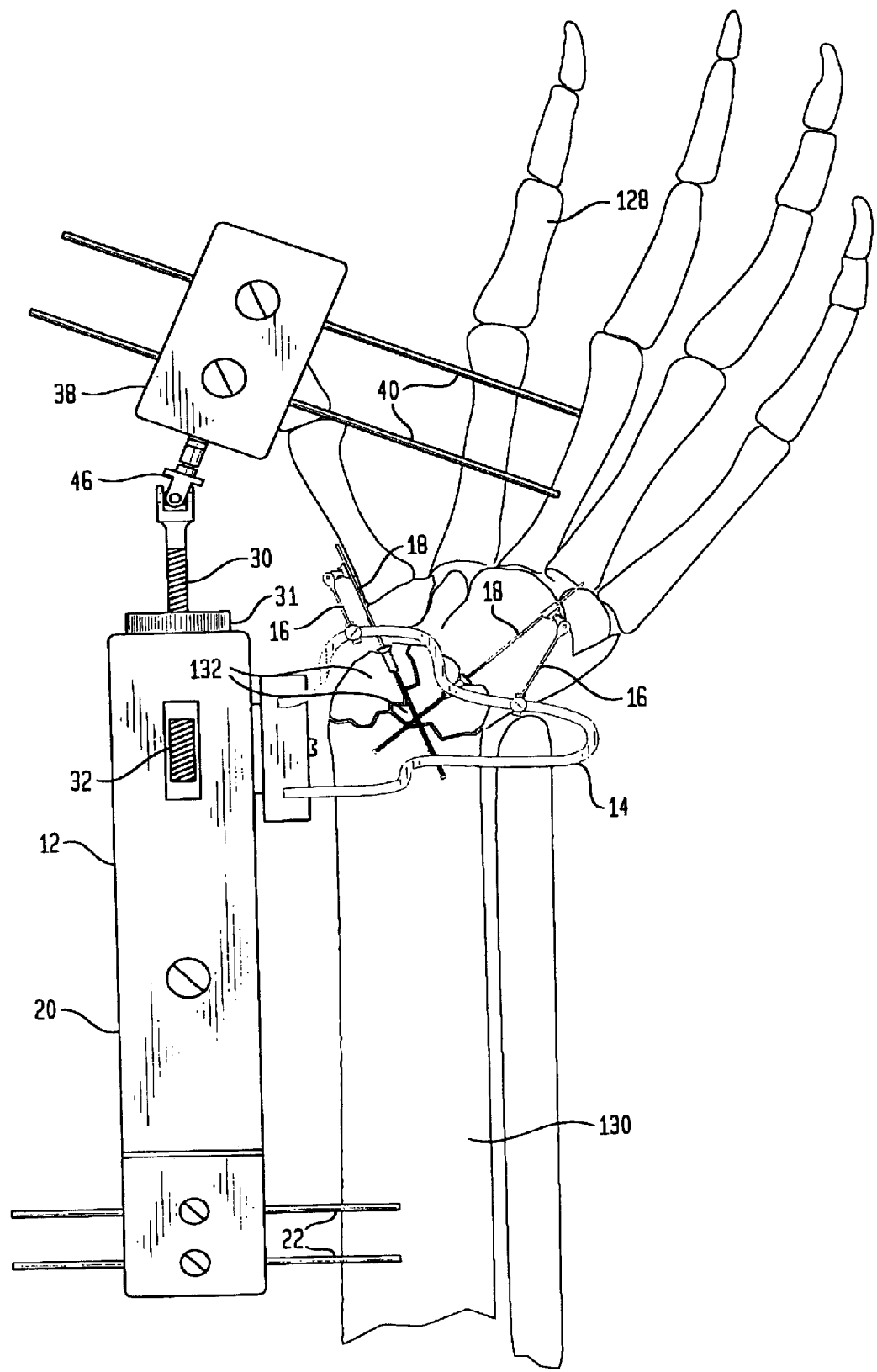
FIG. 6A depicts the fixator assembly as used in the modular fixation of a wrist fracture.

FIG. 6A illustrates the modular fixation of a wrist fracture using the fixator assembly 10. The distractor device 12 of the fixator assembly 10 provides distraction of the fracture. Distraction of the fracture allows for indirect reduction through ligamentotaxis. When the fracture involves the distal radius, the distal and proximal pins 40, 22 of the distractor 12 are respectively placed in the hand metacarpals 128 and the distal ⅓ radius 130. The distal and proximal pin clamp members 38, 20 of the distractor 12 are respectively clamped to the distal and proximal pins 40, 22. Incremental distraction or compression is accomplished by extending or retracting the rod 30 using the thumb screw 31. The universal joint 46 of the distractor 12 enables the distal pin clamp member 38 to be angularly positioned relative to the proximal pin clamp member 20 to fine tune the position of the hand.

Referring still to FIG. 6A, direct fixation of the distal radial fragments 132 is accomplished using the outrigger pins 18 in conjunction with the outrigger pin clamp assemblies 16 and the pin outrigger 14. As the outrigger 14 extends over the wrist joint, the first projecting element 58 generally follows the profile of the distal radius and distal ulna. This enables the outrigger pins 18, which are attached to the first projecting element 58 of the outrigger 14 with the outrigger pin clamp assemblies 16, to be placed obliquely through the distal and proximal radial fragments 132, 130 to fixate and stabilize them. The anatomical configuration of the pin outrigger 14 and the universal articulate motion provided by the outrigger pin clamp assemblies 16 will also allow transverse pin placement through the radial styloid. Outrigger pin placement from dorsal and distal to volar and proximal is also possible. Such pin placement allows the volar tilt of the wrist to be maintained. Outrigger pins 18 may also be secured to the second projecting element 60 for further fixation.

Figure 6B:
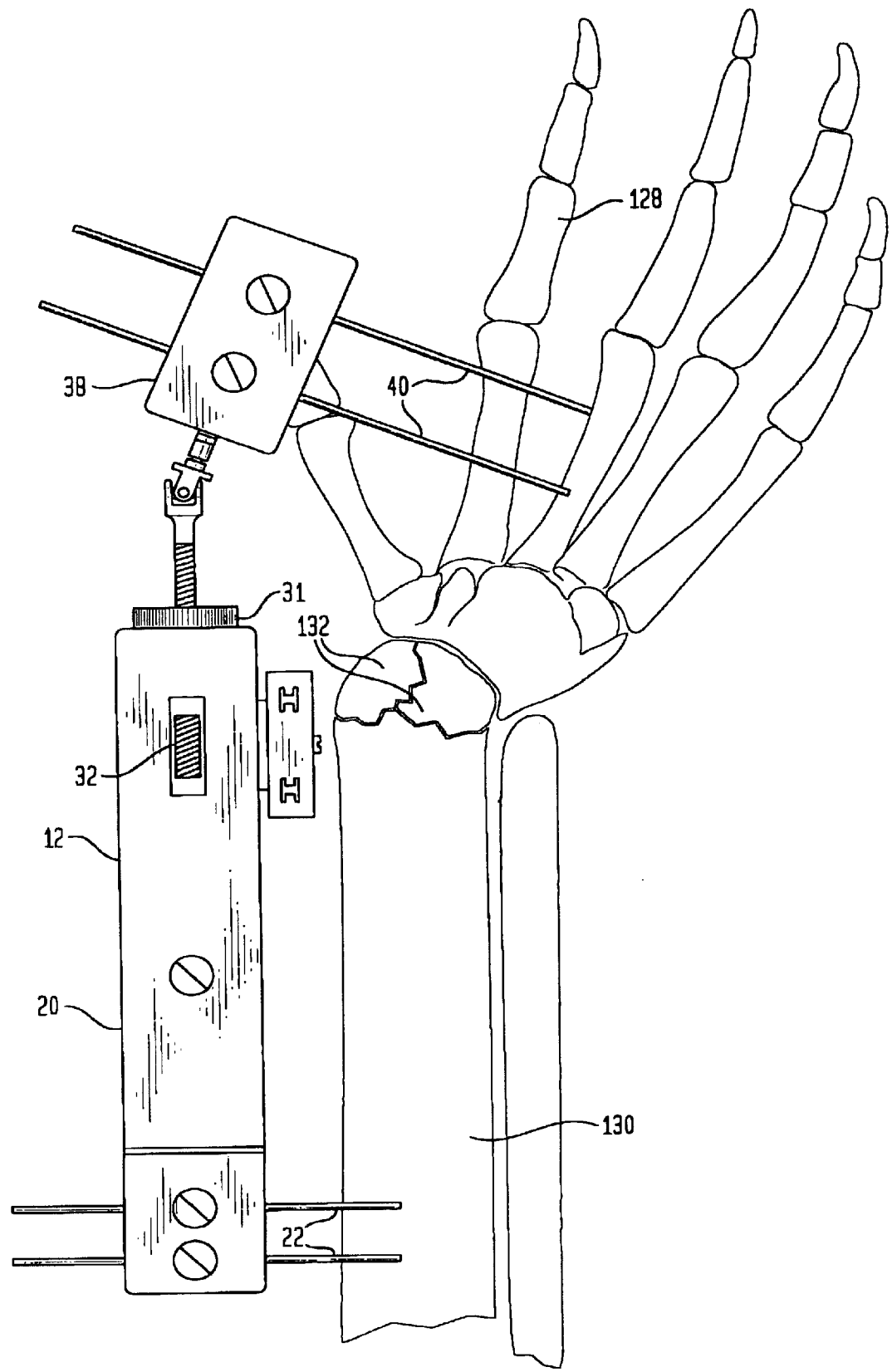
FIG. 6B depicts the distractor device as used in the direct fixation of the distal radius.

FIG. 6B illustrates direct fixation of the distal radius using the distractor device 12 without the outrigger pins and the pin outrigger. Such use of the distractor device 12 is possible with certain types of fracture patterns.

Figure 6C:
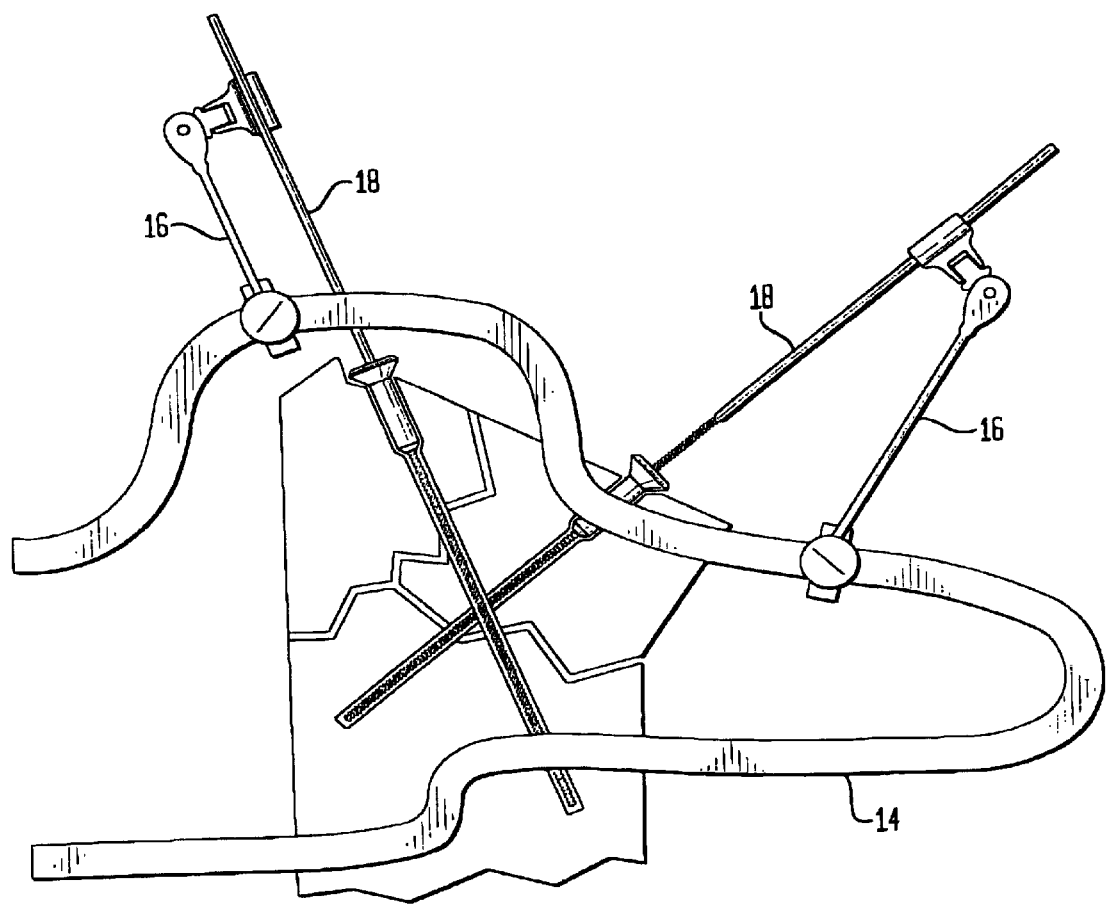
FIG. 6C depicts the outrigger as used in the direct fixation of the distal radius using the outrigger pins and the outrigger pin clamp assemblies.

FIG. 6C illustrates direct fixation of the distal radius using the outrigger pins 18, the pin outrigger 14, and the outrigger pin clamp assemblies 16 without the distractor device. This is possible for fracture patterns which do not require distraction or when distraction is no longer required. Such use allows hand motion at the wrist which has been found extremely desirable during the treatment of such fractures.

The outrigger pins 18 can also be used alone without the outrigger 14 and pin clamp assemblies 16 with certain other types of fractures. Such use of the pins 18 can be made with or without the distractor device depending upon the nature of the fracture.

Figure 7:
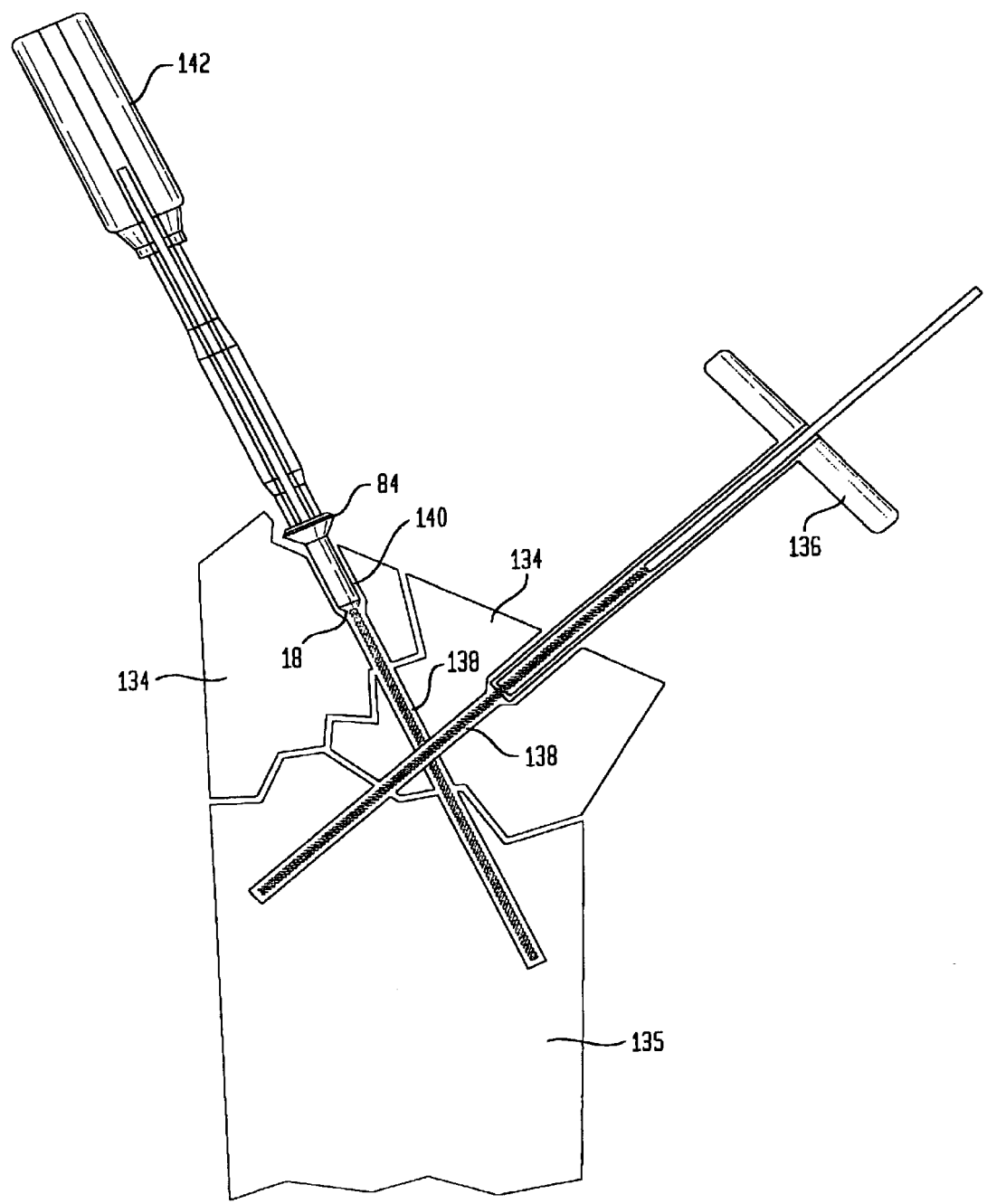
FIG. 7 depicts the outrigger pins as used for providing compression between fracture fragments.

FIG. 7 illustrates compression of the fracture fragments 134, 135 using the outrigger pins 18. If compression of the fracture fragments 134, 135 is desirable, a hand reamer 136 can be used to overdrill the distal bone fragments 134 to open up the hole 138 drilled therein. Compression is provided by driving the screw member 84 of the outrigger pin 18 into the overdrilled hole portion 140 in the distal fragment 134 with a specially adapted screw driver 142. Continued driving of the screw member 84 pushes the distal fragment 134 toward the proximal fragment 135 which is held in place by the threads 90 of the pin member 82.

Figure 8:
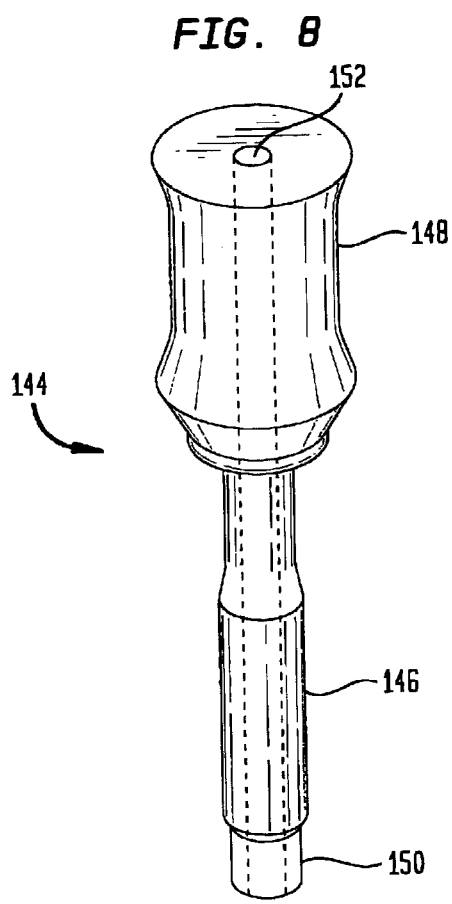
FIG. 8 is partially sectioned, perspective view of a screw driver adapted for driving the screw member of the outrigger pin.

FIG. 8 is a perspective view, partially in section, of a screw driver 144 adapted for driving the screw member of the outrigger pin. The screw driver 144 is similar to the one shown in FIG. 7. The screw driver 144 may include an elongated cylindrical body 146 with a handle 148 disposed at one end and screw member engagement means 150 formed at the other end. An opening 152 (shown with broken lines) extends axially through the body 146 and handle 148 of the screw driver 144. The opening 152 allows entrance of the pin member so that the screw member engagement means 150 of the screw driver 144 can engage the screw driving means of the screw member. In the shown embodiment the screw member engagement means 150 is hexagonally shaped so that it may be received by screw member heads with hexagonally shaped recesses. However, other shapes are possible depending upon the configuration of the screw member's screw driving means.

Figure 9A:
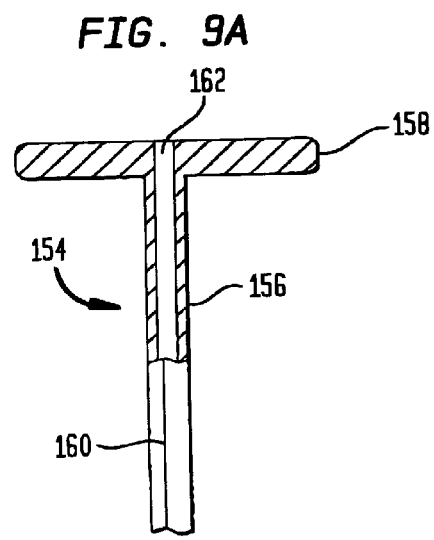
FIG. 9A is an axial cross-sectional view through a hand reamer adapted for use with the outrigger pin.
Figure 9B:
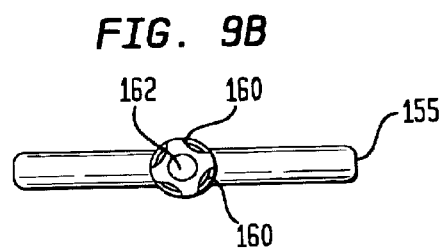
FIG. 9B is an elevational end view of the hand reamer of FIG. 9A.

FIGS. 9A and 9B depict a hand reamer 154 adapted for use with the outrigger pin assembly. The hand reamer 154 is similar to the one shown in FIG. 7. The reamer 154 may be a T-shape member having an elongated cylindrical body 156 with a handle 158 disposed at one end and bone cutting means 160 at the other end. An opening 162 extends axially through the reamer 154 to allow entrance of the pin member of the outrigger pin so that the cutting means 160 of the reamer 154 can engage and overdrill the entrance of the hole drilled in the bone fragment. The cutting means 160 may take the form of a plurality of cutting flutes defined on the outer surface of the cylindrical body 156.

It is understood that the above-described embodiments illustrate only a few of the many possible specific embodiments which can represent applications of the principles of the invention. For example, in some embodiments, the outrigger pins can be conventional transcutaneous pins, wires, or screws. In other embodiments, the pin outrigger may have one or more projecting elements conformed to the anatomy of other bones of the skeleton. Hence, numerous modifications and changes can be made by those skilled in the art without departing from the spirit and scope of the invention.

What is claimed is:

1. A modular fixator assembly for repairing a fractured bone, said fixator assembly comprising:

a distractor device for providing distraction of a fractured bone;

a pin outrigger attached to said distractor device, said outrigger conforming to the anatomical configuration of the fractured bone thereby enabling fixation of fracture fragments of the fractured bone, wherein said outrigger includes a first and second projecting elements, said first projecting element includes a first generally S-shaped section which extends away from said second projecting element and merges with a second generally S-shaped section which extends back toward the second projecting element;

at least one pin for directly fixating the fracture fragments of the fractured bone; and clamping means for attaching said at least one pin to said outrigger.

2. The fixator assembly according to claim 1, wherein said distractor device includes:

a proximal member having means for securing said proximal member to a bone that is proximal to the fracture site;

a distal member having means for securing said distal member to a bone that is distal to the fracture site; and coupling means for selectively varying the distance between said proximal member and said distal member.

3. The fixator assembly according to claim 2, wherein the bone proximal to the fracture site includes the fractured bone.

4. The fixator assembly according to claim 3, wherein the fractured bone includes the radius, the fracture site includes the distal radius, and the bone distal to the fracture site includes a metacarpal bone.

5. The fixator assembly according to claim 2, wherein one of said distal and proximal members of said distractor device includes outrigger mounting means.

6. The fixator assembly according to claim 5, wherein said one of said distal and proximal members including said outrigger mounting means includes slide adjustment means for enabling distal and proximal movement of said outrigger mounting means.

7. The fixator assembly according to claim 1, wherein said outrigger conforms to the anatomical configuration of the distal radius.

8. The fixator assembly according to claim 1, wherein said first projecting element which conforms to the anatomical configuration of the fractured bone.

9. The fixator assembly according to claim 8, wherein the fractured bone includes the distal radius.

10. The fixator assembly according to claim 9, wherein said first projecting element includes a first section which mimics the shape of the radial styloid and a second section which mimics the shape of coronal anatomy of the radius at the level of the wrist joint.

11. The fixator assembly according to claim 1, wherein said second generally S-shaped section converges with said second projecting element.

12. The fixator assembly according to claim 1, wherein said at least one pin includes:

an elongated pin member having an externally threaded portion and an internally threaded screw member removably threaded on said threaded portion of said pin member.

13. The fixator assembly according to claim 12, wherein said pin member includes chuck engaging means for screw driving said threaded portion into a hole drilled in said fracture fragments.

14. The fixator assembly according to claim 12, wherein said screw member includes an enlarged head with a tapered seat.

15. The fixator assembly according to claim 14, wherein said screw member further includes an elongated sleeve that extends from said enlarged head.

16. The fixator assembly according to claim 14, wherein said enlarged head includes screw driving means.

17. The fixator assembly according to claim 14, wherein said pin member extends axially through said screw member.

18. A distractor device for repairing a fractured bone, said distractor device comprising:

a proximal member having means for securing said proximal member to a bone that is proximal to the fracture site;

a distal member having means for securing said distal member to a bone that is distal to the fracture site;

coupling means for selectively varying the distance between said proximal member and said distal member;

a pin outrigger attached to said distractor device, wherein said outrigger includes a first and second projecting elements, said first projecting element includes a first generally S-shaped section which extends away from said second projecting element and merges with a second generally S-shaped section which extends back toward the second projecting element; and outrigger mounting means for mounting a pin outrigger, said outrigger mounting means associated with one of said proximal and distal members.

19. The distractor device according to claim 18, wherein said one of said distal and proximal members associated with said outrigger mounting means includes slide adjustment means for enabling distal and proximal movement of said outrigger mounting means.

20. The distractor device according to claim 18, wherein said coupling means includes an externally threaded bar.

21. The distractor device according to claim 20, wherein said coupling means further includes universal joint means attaching said bar to said distal member.

* * * * *